(12) United States Patent
Gaudin

(10) Patent No.: US 7,741,267 B2
(45) Date of Patent: Jun. 22, 2010

(54) CITRONELLA AND FLORAL PERFUMING INGREDIENT

(75) Inventor: Jean-Marc Gaudin, Annemasse (FR)

(73) Assignee: Firmenich S.A., Geneva (CH)

( * ) Notice: Subject to any disclaimer, the term of this patent is extended or adjusted under 35 U.S.C. 154(b) by 762 days.

(21) Appl. No.: 11/616,160

(22) Filed: Dec. 26, 2006

(65) Prior Publication Data

US 2007/0105749 A1 May 10, 2007

Related U.S. Application Data

(63) Continuation of application No. PCT/IB2005/002112, filed on Jul. 20, 2005.

(30) Foreign Application Priority Data

Aug. 4, 2004 (WO) .................. PCT/IB2004/ 02557

(51) Int. Cl.
 *A61K 8/18* (2006.01)
 *A61Q 13/00* (2006.01)
 *C11D 3/50* (2006.01)
(52) U.S. Cl. ................ 512/24; 512/1; 512/23
(58) Field of Classification Search ...................... 512/1, 512/16, 17, 23, 24
See application file for complete search history.

(56) References Cited

U.S. PATENT DOCUMENTS 4,649,044 A * 3/1987 Gomi et al. .................. 424/49

OTHER PUBLICATIONS

English Abstract (JP 02 188549)—XP002363409 P. Hiroaki et al., "Fragrance compositions containing 2-(alkylcyclohexyl)-1-propanals" (1990).
S. Arctander, XP009060131, "Perfume And Flavor Chemicals", Aroma Chemicals, pp. 273, (1969).
E. Brenna et al., XP004404149, "Enantioselective perception of chiral odorants", Tetrahedron: Asymmetry, vol. 14, No. 1, pp. 1-42 (2003).

* cited by examiner

*Primary Examiner*—James Seidleck
*Assistant Examiner*—Saira Haider
(74) *Attorney, Agent, or Firm*—Winston & Strawn LLP

(57) ABSTRACT

The present invention relates to a perfuming ingredient of a compound of formula

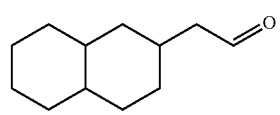

(I)

in the form of any one of its isomers or of a mixture thereof, and having a boiling point above 250° C., as measured at a pressure of 1013 mbar and its use in a method to confer, enhance, improve or modify the odor properties of a perfuming composition or perfumed article. The perfuming compositions and perfumed articles having the desirable odor characters are also part of this invention.

9 Claims, No Drawings

CITRONELLA AND FLORAL PERFUMING INGREDIENT

CROSS-REFERENCE TO RELATED APPLICATIONS

This application is a continuation of International application PCT/IB2005/002112 filed Jul. 20, 2005, the entire content of which is expressly incorporated herein by reference thereto.

TECHNICAL FIELD

The present invention relates to the field of perfumery and in particular to the use as perfuming ingredient of a compound of formula

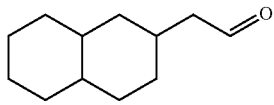
(I)

in the form of any one of its isomers or of a mixture thereof, and having a boiling point above 250° C., as measured at a pressure of 1013 mbar.

BACKGROUND

Compounds having a strong tenacity and an odor of the type white flower and citronella are very rare and very much prized by perfumers. Indeed, compounds having such an odor are especially useful, inter alia, in functional perfumery. However, in the vast majority of the cases the compounds suffer from a lack of tenacity which renders them of little use in functional perfumery.

It is the aim of this application to solve the problem by providing a compound having a floral and citrus/citronella odor, while having a sufficient tenacity to allow its use also in functional perfumery.

To the best of our knowledge the invention's compound has been only reported in the book by S. Arctander, "Perfume and Flavor Chemicals", 1969, Montclair, N.J., USA. In the book, the invention's compound has been mentioned under the reference number 825 and the name of decahydro-beta-naphthylacetaldehyde.

However, the compound mentioned by Arctander's is described as having a boiling point of 236° C. and an odor of the type "semi-dry, musty-woody with a remote resemblance to notes in ambergris" and "a tenacity very poor". Moreover, it is also stated that "the author believes that this material has little or no interest to the perfume industry".

Therefore, Arctander's disclosure suggests only an odor, a tenacity and an interest in such compound which is at the opposite of what is aimed in the present invention, and is far from suggesting that a compound of formula (I) can be used as perfuming ingredient to impart flower/citrus notes.

SUMMARY OF THE INVENTION

The present invention now relates about the use in perfumery of a compound of formula

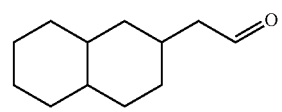
(I)

in the form of any one of its isomers or of a mixture thereof, and having a boiling point above 250° C. The present invention concerns also the compositions or articles associated with the compound.

DETAILED DESCRIPTION OF THE PREFERRED EMBODIMENTS

We have now surprisingly discovered that the compound of formula

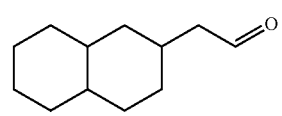
(I)

in the form of any one of its isomers or of a mixture thereof, and having a boiling point comprised between 245° C. and 264° C., as measured at a pressure of 1013 mbar; is a useful perfuming ingredient with a very good tenacity and which, unexpectedly, imparts odor notes of the floral and/or citrus, citronella type.

The compound of formula (I) possesses three asymmetric carbon atoms, and the decaline group can have a cis or trans conformation, so as to adopt the following structures:

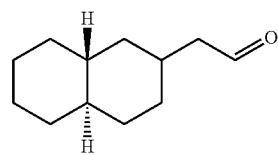
(I-trans)

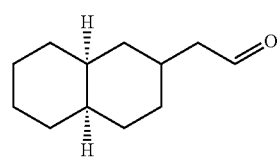
(I-cis)

wherein the hydrogen atoms are in a relative configuration. Therefore, as mentioned above, the compound of formula (I) can be in the form of any one of its diastereoisomers or stereoisomers.

According to a preferred embodiment of the invention, the compound of formula (I) has a boiling point comprised between 246° C. and 253° C., as measured at a pressure of 1013 mbar.

Furthermore, according to another embodiment, the compound (I) is in the form of a mixture containing less than 50% w/w of isomer (I-trans) and more than 50% w/w of isomer (J-cis). More preferably, the mixture contains less than 30% w/w of (I-trans) and more than 70% w/w of (I-cis).

As mentioned above, surprisingly, it has been found that the typical odor of the invention's compound contributes to the fragrance of composition, or perfumes, having an aldehyde, white flowers and/or citrus, citronella fragrance character or nature.

In particular, an invention's mixture containing between 70 and 80% of isomer (I-cis) and between 30 and 20% of isomer (I-trans) possesses an aldehydic and flowery note together with a citrusy and citronella note. The flowery note is of the white flower-lilly of the valley-type and is also slightly linden. The citrusy note possesses a very natural citrus white peel aspect.

The overall odor of this mixture is quite powerful and possesses also a tenacity and a long lastingness which are high for these odors notes. The perfuming properties allow an easy use of the invention's mixture in any field of functional perfumery, as well as of fine perfumery.

The pure cis or trans isomers according to the invention have similar odors and properties, although they possess a proper character. Isomer (I-cis), compared to the above mixture, is a bit fresher and has a citronella note more developed, while isomer (I-trans) is less powerful.

The invention concerns also the use of a compound of formula (I) as perfuming ingredients, in particular to confer, enhance, improve or modify the aldehyde, white flowers and/or citrus character of a perfuming composition. In other words, it concerns a method to confer, enhance, improve or modify the odor properties of a perfuming composition or perfumed article, which method comprises adding to the composition or article an effective amount of a compound of formula (I). The method is particularly useful for conferring, enhancing, improving or modifying the aldehyde, white flowers and/or citrus notes to, or of, the perfuming composition or perfumed article. Therefore it is particularly useful for the perfuming compositions or perfumed articles having an aldehyde, white flowers and/or citrus character.

By "use of a compound of formula (I)" it has to be understood here also the use of any composition containing the compound (I) and which can be advantageously employed in the perfumery industry as active ingredients.

The compositions, which are in fact perfuming compositions that can be advantageously employed as perfuming ingredients, are also embodiments of the present invention. Therefore, a preferred embodiment of the present invention is a perfuming composition comprising:
i) as perfuming ingredient, a compound of formula (I) as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. The carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials, for example, may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's Verlag-GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation techniques.

Generally speaking, by "perfumery base" we mean here a composition comprising at least one perfuming co-ingredient.

The perfuming co-ingredient is not of the formula (I). Moreover, by "perfuming co-ingredient" it is meant here a compound, which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitrites, terpene hydrocarbons, nitrogenous or sulphurous heterocyclic compounds and essential oils, and the perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that the co-ingredients may also be compounds known to release in a controlled manner various types of perfuming compounds.

For the compositions which comprise both a perfumery carrier and a perfumery base, other suitable perfumery carrier than those previously specified can be also ethanol, water/ethanol mixtures, limonene or other terpenes, isoparaffins such as those known under the trademark ISOPAR® (origin: Exxon Chemical) or glycol ethers and glycol ether esters such as those known under the trademark DOWANOL® (origin: Dow Chemical Company).

Generally speaking, by "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that the ingredients are well known to a person skilled in the art.

Preferred perfuming compositions are those having an aldehyde, white flowers and/or citrus character.

An invention's composition consisting of a compound of formula (I) and at least one perfumery carrier represents a particular embodiment of the invention as well as a perfuming composition comprising a compound of formula (I), at least one perfumery carrier, at least one perfumery base, and optionally at least one perfumery adjuvant.

Its is also understood here that, unless otherwise indicated or described, any mixture resulting directly from a chemical synthesis, e.g. without an adequate purification, in which the compound of the invention would be involved as a starting intermediate or end-product could not be considered as a perfuming composition according to the invention.

Furthermore, in view of its unexpected tenacity and odor properties, the compounds of formula (I) are particularly useful in all the fields of modern perfumery to positively impart or modify the odor of a consumer product into which the compound of formula (I) is added. In particular to impart an aldehyde, white flowers and/or citrus character to the fragrance of the consumer product.

Consequently, a perfumed article comprising:
i) as perfuming ingredient, a compound of formula (I) or an invention's composition; and
ii) a consumer product base, is also an embodiment of the present invention.

For the sake of clarity, it has to be mentioned that, by "consumer product base" we mean here a consumer product which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of the product.

Examples of suitable consumer products include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. As detergents there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention compound, so that it may be necessary to protect the latter from premature decomposition, for example by encapsulation.

The proportions in which the compound of formula (I) according to the invention can be incorporated into the various aforementioned articles or compositions vary within a wide range of values. These values are dependent on the nature of the article to be perfumed and on the desired organoleptic effect as well as on the nature of the co-ingredients in a given base when the compounds according to the invention are mixed with perfuming co-ingredients, solvents or additives commonly used in the art.

For example, in the case of perfuming compositions, typical concentrations are in the order of 0.001% to 10% by weight, or even more, of the compounds of the invention based on the weight of the composition into which they are incorporated. Concentrations lower than these, such as in the order of 0.01% to 5% by weight, can be used when these compounds are incorporated into perfumed articles.

The compound of formula (I) is obtainable by a process comprising the following steps:

a) the reaction of 2-decalone, in the form of any one of its isomers or of a mixture thereof, with an appropriate Witting reagent, such as $Me_3PCH_2COOMe$;
b) reducing the unsaturated ester obtained in step 2 into the corresponding saturated ester, for example by means of a hydrogenation;
c) reducing the saturated ester into the saturated alcohol, for example by means of an aluminum hydride; and
d) oxidizing the alcohol obtained in step c) into the desired aldehyde, for example by means of a derivative of TEMPO.

The above-mentioned process is illustrated in a particular embodiment in the Examples.

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^3H$ and $^{13}C$, the chemical displacements δ are indicated in ppm with respect to TMS as standard, the coupling constants J are expressed in Hz.

Example 1

Synthesis of Compounds of Formula (I)

The starting material 2-decalone, was purchased from Aldrich SA (mixture 20/80 of trans/cis 2-decalone).

Pure cis or trans 2-decalone have been obtained by a distillation of 2-decalone on a Fisher column (1.4 mbar, bath 93° C., B.p. 58° C. for the trans, 10-15° higher for the cis).

General Procedure a) Formation of the Unsaturated Ester Intermediate

A 1 L three-neck flask was charged with the required 2-decalone (50 g, 328 mmoles), methyl (dimethoxyphosphoryl)acetate (77.6 g, 426 mmoles) and 300 ml of cyclohexane. Then 71 g of a 30% w/w MeONa solution in MeOH was added over a period of 30 minutes. The temperature was maintained around 40° C. with a water bath. After an additional period of 30 minutes, the reaction mixture was poured into cold water (200 ml) containing 10 ml of acetic acid. The organic phase was washed with water and the solvent removed under vacuum. The crude product (70 g) was used for the next step without further purification.

b) Reduction of the Unsaturated Ester into the Saturated Ester

The product obtained in step a) (70 g) and 2 g of Pd—C 5% was put under 1 atmosphere of hydrogen overnight. After filtration, the crude product thus obtained was used for the next step without further purification.

c) Reduction of the Saturated Ester into the Saturated Alcohol

A 2 liter three-neck flask was charged with lithium aluminum hydride (8 g, 210 mmoles) and 800 ml of dry diethylether. To this solution was added dropwise a solution of the product obtained in step b) (70 g) in 100 ml of ether, during the addition the temperature of the reaction medium was kept at around 30° C.

The reaction was then carefully hydrolyzed with 60 ml of water, stirred 1 hour at room temperature and filtered over CELITE. The solvent was removed under vacuum and the product rapidly distilled under reduced pressure (Kugelrohr distillation, bp: 85°-90° C./0.2 mbar). 52 g of pure product were obtained (overall yield of approximately 85% from 2-decalone (3 steps)).

d) Oxidation of the Saturated Alcohol into Compound of Formula (I)

A 1.5 L three-neck flask was charged with PIPO (1.17 g, see R. A. Sheldon et al., in Synlett 2001, 102), sodium bromide (0.14 g), of the alcohol obtained in step c) (24.5 g, 134 mmoles) and 170 ml of ethyl acetate. After dissolution of PIPO, to the reaction mixture there was added, over 90 minutes, an aqueous solution of NaOCl (100 g-12% solution, approx 1.1 eq) and containing also containing 2 g of sodium bicarbonate. During the addition, the temperature of the reaction medium was maintained at around 25° C. After an additional period of 30 minutes, the two phases reaction mixture was decanted. The organic phase was washed with water and the solvent removed under vacuum to obtain 22 g of crude product. A distillation under reduced pressure provided the desired compound (purity >94-95% as measured by GC).

Compound of Formula (I-Trans)

starting from pure trans 2-decalone the desired compound was obtained in the form of a mixture of two isomers (65/35):

Boiling point=261° C. at 1013 mbar

MS (most important peaks): 180 (7,M+), 136 (100) (identical for the both isomers)

$^{13}$C NMR (for the mixture): 26.52, 26.62, 28.10, 30.15, 32.85, 33.23, 33.61, 33.73, 33.87, 33.90, 34.07, 37.39, 37.81, 40.65, 42.84, 42.91, 43.56, 46.46, 51.42, 202.80, 203.02

$^3$H NMR (for the mixture): 9.75 (1H, t, J=1 Hz); 2.48 (1H, m); 2.28 (1H, dd, J=6 Hz, J=1 Hz); 1.92 (1H, m); 1.7 (3H, m); 1.57 (4H, m); 1.5 (1 H, m); 1.40 (1H, m); 1.22 (2H, m); 0.7-1.15 (5H, m)

Compound of Formula (I-Cis)

starting from pure cis 2-decalone the desired compound was obtained in the form of a mixture of two isomers (80/20):

Boiling point=247° C. at 1013 mbar

MS (most important peaks): 180 (2), 136 (100) (identical for the both isomers)

$^{13}$C NMR (major isomer): 20.90 (t), 25.72 (t), 26.98 (t), 27.68 (t), 32.11 (t), 32.23 (t), 32.60 (t), 33.25 (d), 35.43 (d), 35.89 (d), 51.60 (t), 202.85 (d).

$^{13}$C NMR (minor isomer): 21.5, 25.60, 26.64, 27.27, 33.47, 33.63, 33.74, 33.92, 35.76, 40.67, 51.43, 202.92

$^3$H NMR (for the mixture): 9.75 (1H, t, J=1 Hz); 2.30 (1H, dd, J=6 Hz, J=1 Hz); 2.27 (1H, m); 1.92 (1H, m); 1.7 (4H, m); 1.50 (4H, m); 1.4 (3H, m); 1.15-1.35 (5H, m)

Compound of Formula (I) in the Form of a (I-Cis)/(I-Trans) Mixture (80/20)

starting from pure commercial 2-decalone (Aldrich SA) the desired mixture was obtained in the form of a (80/20) mixture of isomers (I-cis)/(I-trans):

Boiling point=249° C. at 1013 mbar

MS (most important peaks): 180 (2), 136 (100) (identical for the both isomers)

The $^{13}$C NMR and $^3$H NMR spectra are best described by the sum of the above-mentioned spectra.

Example 2

Preparation of a Perfuming Composition

A perfuming composition of the citrus-herbaceous type, for a liquid detergent, was prepared by admixing the following ingredients:

| Ingredient | Parts by weight |
| --- | --- |
| Amyl acetate | 60 |
| 50%* Aldehyde C8 | 40 |
| 50%* Aldehyde C9 | 50 |
| 50%* Aldehyde C10 | 20 |
| Hexylcinnamic aldehyde | 250 |
| Allyl amyl glycolate | 30 |
| Verdyl acetate | 350 |
| 10%* Ethyl butyrate | 30 |
| Camphor | 140 |
| (−)-(R)-1(6),8-p-Menthadien-2-one | 10 |
| 10%* Damascone alpha[1] | 20 |
| DOREMOX ®[2] | 40 |
| Eucalyptus Globulus | 70 |
| 10%* Ehtyl-2-Methylbutytate | 30 |
| HEDIONE ®[3] | 100 |
| Geraniol | 100 |
| 10%* Geranyl Nitrile | 70 |
| Litsea Cubeba essential oil | 60 |
| 10%* OZONIL ®[4] | 40 |
| Orange essential oil | 1200 |
| Methyl salicylate | 20 |
| 1,4(8)-P-menthadiene | 100 |
| 2-Isopropyl-5-methylphenol | 10 |
| 2,4-Dimethyl-3-cyclohexen-1-carboxaldehyde[5] | 30 |
| 1,4-Cineole | 30 |
| | 2900 |

*in dipropyleneglycol
[1]origin: Firmenich SA, Geneva, Switzerland
[2]tetrahydro-4-methyl-2-phenyl-2H-pyran; origin: Firmenich SA, Geneva, Switzerland
[3]methyl dihydrojasmonate; origin: Firmenich SA, Geneva, Switzerland
[4]mixture of 2/3-tridecenenitrile; origin: H&R, Germany
[5]origin: International Flavors & Fragrances, USA The addition of 100 parts by weight of the inventive mixture, in the form of a mixture containing 80% of (I-cis) and 20% of (I-trans), to the above-described functional composition imparted to the latter a "clean", aldehyde and lily of the valley connotation. The overall effect obtained by the addition of the inventive compound is best described by a boost of the citrus notes of the functional composition as well as a strong decrease of the fatty aspect given by the nitrile. No dry, musty-woody or ambergris notes have been imparted by the addition of the inventive compound.

Example 3

Preparation of a Perfuming Composition

A perfuming composition of the citrus-floral type, for a soap, was prepared by admixing the following ingredients:

| Ingredient | Parts by weight |
| --- | --- |
| Benzyl dimethyl carbinol acetate | 80 |
| Benzyl acetate | 60 |
| Linalyl acetate | 200 |
| Styrallyl acetate | 50 |
| 10%* Aldehyde C 10 | 20 |
| Hexylcinnamic aldehyde | 220 |
| 50%* Aldehyde MNA[1] | 20 |
| Aldehyde Supra[1] | 30 |
| 10%* Methyl Benzoate | 10 |
| 10%* CETALOX ®[2] | 40 |
| 10%* Raspberry ketone | 30 |
| 1%* Cis-3-hexenol | 20 |
| Citronellol | 100 |
| 4-Cyclohexyl-2-methyl-2-butanol[1] | 80 |
| Coumarine | 20 |

-continued

| Ingredient | Parts by weight |
|---|---|
| Cyclamen Aldehyde | 40 |
| Allyl cyclohexylpropionate | 20 |
| 10%* α-Damascone[1] | 40 |
| Eugenol | 40 |
| (1'R,2R)-2-Methyl-4-(2',2',3'-trimethyl-3'-cyclopenten-1'-yl)-4-penten-1-ol[1] | 30 |
| HABANOLIDE ®[3] | 100 |
| HEDIONE ®[4] | 100 |
| Heliotropine | 20 |
| IRALIA ®[5] Total | 200 |
| LILIAL ®[6] | 100 |
| Linalol | 200 |
| Methyl naphtyl ketone | 80 |
| 1%* Rose oxide | 10 |
| Patchouli essential oil | 100 |
| Orange essential oil | 50 |
| Verdyl propionate | 50 |
| p-tert-Butylcyclohexyl acetate | 300 |
| 2,2,2-Trichloro-1-phenylethyl acetate | 80 |
| Benzyl salicylate | 300 |
| 10%* Methyl salicylate | 40 |
| TerpinEol | 100 |
| Vert de Lilas | 20 |
| | 3000. |

*in dipropyleneglycol
[1] origin: Firmenich SA, Geneva, Switzerland
[2] dodecahydro-3a,6,6,9a-tetramethyl-naphtho[2,1-b]furan; origin: Firmenich SA, Geneva, Switzerland
[3] pentadecenolide; origin: Firmenich SA, Geneva, Switzerland
[4] methyl dihydrojasmonate; origin: Firmenich SA, Geneva, Switzerland
[5] methyl ionone; origin: Firmenich SA, Geneva, Switzerland
[6] 3-(4-tert-butylphenyl)-2-methylpropanal; origin: Givaudan-Roure SA, Vernier, Suisse The addition of 50 parts by weight of the inventive mixture cited in Example 2, to the above-described floral-citrus functional composition imparted to the latter a strong fresh-lily of the valley note, slightly citrus, which could not be obtained by the addition of any of the known perfuming aldehyde. The fragrance of the composition thus obtained has also a quite clean aldehydic-citronellal connotation. As for the above example, no dry, musty-woody or ambergris notes have been imparted by the addition of the inventive compound.

What is claimed is:

1. A compound of formula

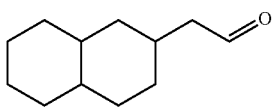
(I)

in the form of any one of its isomers or of a mixture thereof, and having a boiling point comprised between 245° C. and 264° C., as measured at a pressure of 1013 mbar, and said compound is in the form of a mixture containing less than 30% w/w of isomer (I-trans) and more than 70% w/w of isomer (I-cis), and wherein said isomers are of formula

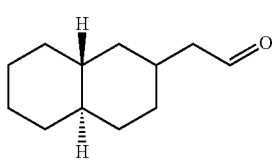
(I-trans)

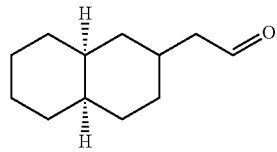
(I-cis)

wherein the hydrogen atoms are in a relative configuration.

2. A compound according to claim 1, wherein the compound has a boiling point of between 246° C. and 253° C., as measured at a pressure of 1013 mbar.

3. A method to confer, enhance, improve or modify the odor properties of a perfuming composition or perfumed article, which method comprises adding to the composition or article an odor effective amount of a compound of formula (I)

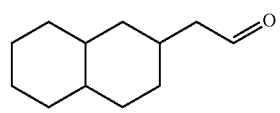
(I)

in the form of any one of its isomers or of a mixture thereof, and having a boiling point comprised between 245° C. and 264° C., as measured at a pressure of 1013 mbar, and said compound is in the form of a mixture containing less than 30% w/w of isomer (I-trans) and more than 70% w/w of isomer (I-cis), and wherein said isomers are of formula

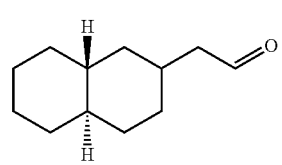
(I-trans)

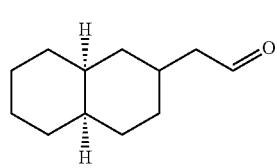
(I-cis)

wherein the hydrogen atoms are in a relative configuration.

4. A method according to claim 3, wherein it is conferred, enhanced, improved or modified the aldehyde, white flowers and/or citrus character of the perfuming composition or perfumed article.

5. A perfuming composition comprising
   i) at least one compound of formula (I) as defined in claim 1;
   ii) at least one ingredient selected from the group consisting of a perfumery carrier and a perfumery base; and
   iii) optionally at least one perfumery adjuvant.

6. A perfumed article comprising:
   i) an odor effective amount of at least one compound of formula (I)

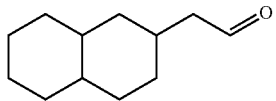 (I)

in the form of any one of its isomers or of a mixture thereof, and having a boiling point comprised between 245° C. and 264° C., as measured at a pressure of 1013 mbar, and said compound is in the form of a mixture containing less than 30% w/w of isomer (I-trans) and more than 70% w/w of isomer (I-cis), and wherein said isomers are of formula

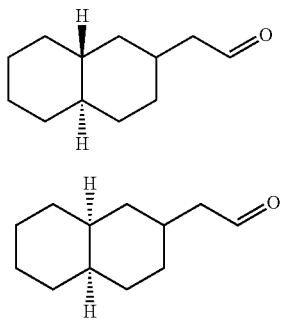

wherein the hydrogen atoms are in a relative configuration; and ii) a consumer product base.

7. A perfumed article according to claim 6, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

8. A perfumed article comprising:

i) at least one composition as defined in claim 4; and ii) a consumer product base.

9. A perfumed article according to claim 8, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

\* \* \* \* \*

UNITED STATES PATENT AND TRADEMARK OFFICE
CERTIFICATE OF CORRECTION

PATENT NO. : 7,741,267 B2 Page 1 of 1
APPLICATION NO. : 11/616160
DATED : June 22, 2010
INVENTOR(S) : Gaudin It is certified that error appears in the above-identified patent and that said Letters Patent is hereby corrected as shown below:

Title Page:
Item (73) Assignee, after "Firmenich" change "S.A." to -- SA --.

Signed and Sealed this

Third Day of August, 2010

David J. Kappos
*Director of the United States Patent and Trademark Office*